United States Patent [19]

Grollimund et al.

[11] Patent Number: 5,448,365
[45] Date of Patent: Sep. 5, 1995

[54] SYSTEMS FOR OPTICAL INSPECTION

[75] Inventors: Gary E. Grollimund, Chesterfield; Herbert C. Longest, Jr., Midlothian; Barry S. Smith, Hopewell, all of Va.; Roy E. VanDerLinden, Frederick, Md.

[73] Assignee: Philip Morris Incorporated, New York, N.Y.

[21] Appl. No.: 108,122

[22] Filed: Aug. 17, 1993

Related U.S. Application Data

[63] Continuation-in-part of Ser. No. 884,746, May 15, 1992.

[51] Int. Cl.$^6$ ............................................ G01N 21/89
[52] U.S. Cl. ................................. 356/430; 250/239; 250/559.42
[58] Field of Search ............... 356/237, 430; 250/562, 250/572, 239; 348/373, 374, 375, 376, 49

[56] References Cited

U.S. PATENT DOCUMENTS

| | | | |
|---|---|---|---|
| 2,446,628 | 8/1948 | Brown | 209/587 |
| 2,936,886 | 5/1960 | Harmon | 209/587 |
| 3,034,645 | 5/1962 | Groppe | 209/536 |
| 3,040,179 | 6/1962 | Bolt | 250/223 |
| 3,447,679 | 6/1969 | Molins et al. | 209/535 |
| 3,557,374 | 1/1971 | Schmermund | 131/908 |
| 3,703,235 | 11/1972 | McEnery | 209/585 |
| 3,784,738 | 1/1974 | Natter | 348/49 |
| 4,011,950 | 3/1977 | McLoughlin et al. | 209/536 |
| 4,025,201 | 5/1977 | Deane | 209/939 |
| 4,208,578 | 6/1980 | McLoughlin et al. | 250/214 AG |
| 4,266,674 | 5/1981 | Bell et al. | 209/536 |
| 4,280,624 | 7/1981 | Ford | 209/585 |
| 4,377,743 | 3/1983 | Bolt et al. | 250/223 R |
| 4,398,546 | 8/1983 | Fisher et al. | 131/88 |
| 4,410,278 | 10/1983 | Makihira et al. | 356/445 |
| 4,568,970 | 2/1986 | Rockstead | 348/49 |
| 4,574,958 | 3/1986 | Manservisi | 209/535 |
| 4,579,455 | 4/1986 | Levy et al. | 356/394 |
| 4,639,592 | 1/1987 | Heitmann | 250/223 B |
| 4,645,921 | 2/1987 | Heitmann et al. | 209/536 |
| 4,652,133 | 3/1987 | Antoszewski et al. | 356/376 |
| 4,687,107 | 8/1987 | Brown et al. | 209/587 |
| 4,767,924 | 8/1988 | Giebel et al. | 250/223 R |
| 4,907,607 | 3/1990 | Focke et al. | 131/908 |
| 4,955,948 | 9/1990 | Focke et al. | 209/536 |
| 5,013,905 | 5/1991 | Neri | 209/536 |
| 5,034,822 | 7/1991 | Stevens | 348/373 |
| 5,127,737 | 7/1992 | Neri | 356/237 |
| 5,153,668 | 10/1992 | Katzir et al. | 356/237 |
| 5,175,717 | 12/1992 | Saimi et al. | 359/507 |

FOREIGN PATENT DOCUMENTS

| | | | |
|---|---|---|---|
| 472280 | 2/1929 | Germany | 209/111.5 |
| 2221029 | 1/1990 | United Kingdom . | |

OTHER PUBLICATIONS

Haehner, C. B. "Inspection System for Round Objects", Western Electric Technical Digest, No. 6 (Apr. 1967) pp. 29-30.

Primary Examiner—Richard A. Rosenberger
Attorney, Agent, or Firm—Kevin B. Osborne; James E. Schardt; Charles E. B. Glenn

[57] ABSTRACT

Improved systems for optical inspection are provided. The improved systems use modified camera boxes to provide increased, and more uniform, illumination of the objects being inspected through the use of illuminator windows. The lens arrangement of the improved camera boxes is contained within a self-contained, sealed housing that is separate from the camera to prevent particle contamination of the lens arrangement and provide improved flexibility during installation of the camera boxes on the inspection systems. The self-contained housing also provides for a reduction in the space required for the camera boxes. The light receiver of the housing is provided with the capability for preventing particle contamination of the receiver itself.

33 Claims, 12 Drawing Sheets

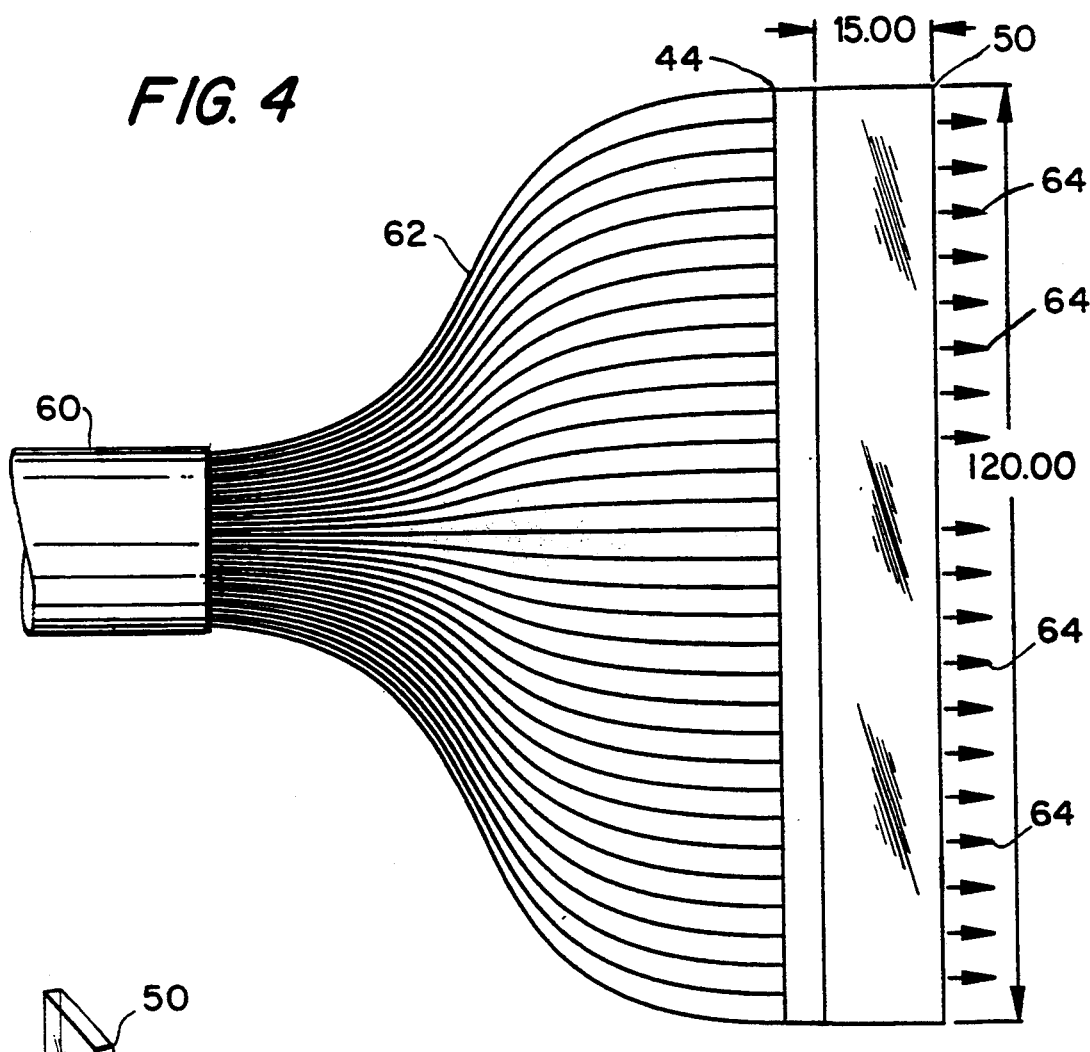
FIG. 4
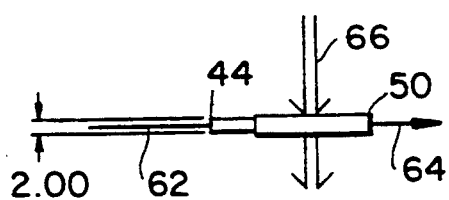
FIG. 5
FIG. 6

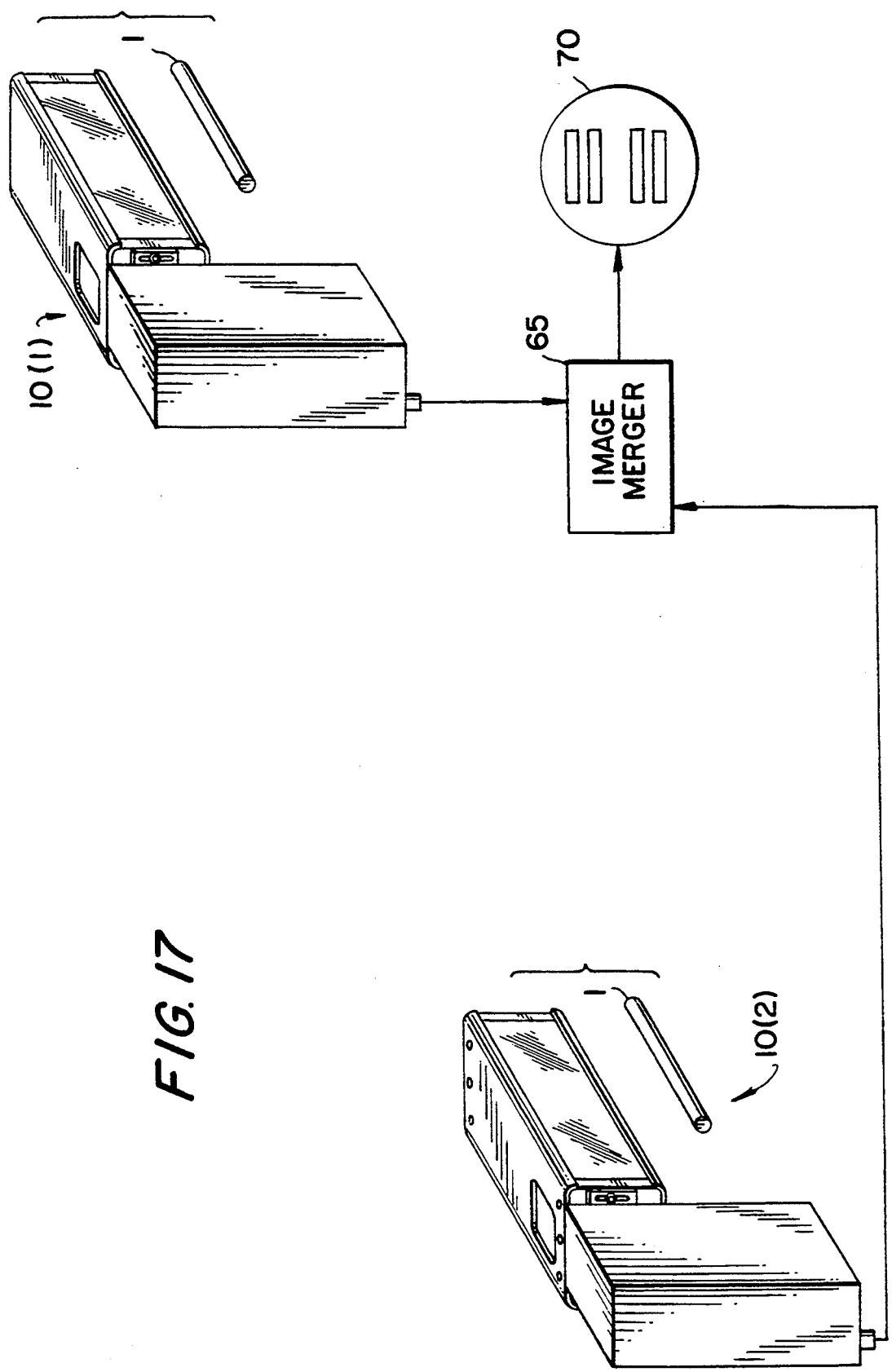

SYSTEMS FOR OPTICAL INSPECTION

CROSS REFERENCE TO RELATED APPLICATION

This application is a continuation-in-part of copending, commonly-assigned United States patent application Serial No. 07/884,746, filed May 15, 1992, which is hereby incorporated by reference in its entirety.

BACKGROUND OF THE INVENTION

The present invention relates to systems for optical inspection. More particularly, this invention relates to camera boxes used in systems for optically inspecting cylindrical surfaces such as the cylindrical surfaces of cigarettes.

Systems for optically inspecting cylindrical surfaces are described by the above-incorporated, commonly-assigned United States patent application Ser. No. 07/884,746, filed May 15, 1992. That application describes optical inspection systems that operate by first inspecting at least 180° of the circumference of a first side, and then inspecting at least 180° of the circumference of the other side. The inspection systems illuminate more than 180° of the circumference of the object by utilizing two, angularly spaced, light sources. Images of the illuminated object are then formed (using camera boxes and computer processors), which images are analyzed using various techniques to make possible the detection of very small defects, as well as to compensate for possible nonuniform illumination of the objects in the circumferential direction.

A possible disadvantage of the camera boxes of the above-incorporated patent application is the large size required, due to the fact that the camera boxes contain a conventional video camera, two lights sources, and a series of apertures and reflectors which are used to form the image. A further possible disadvantage of the camera boxes is the system installation limitation due to the straight in-line nature of the conventional video camera. These disadvantages may result in requiring extra intermediate drums to provide adequate installation space for the camera boxes, in addition to the overall increased space requirements of the inspection system itself.

Another possible disadvantage of the camera boxes of the above-incorporated application is the fact that the camera boxes are not sealed units. The aperture design of the camera boxes is such that it may permit particle contamination of the optics, and the camera itself, to occur. Such contamination may occur due to the nature of the manufacturing operation (e.g., production rates approaching 10,000 cigarettes a minute may cause loose tobacco fibers and ,other contaminants to be introduced into the manufacturing environment).

A further possible disadvantage of the camera boxes of the above-incorporated application is the ability to sufficiently illuminate the object during inspection. The inspection system may utilize additional image processing techniques to compensate for possible nonuniform illumination of the objects in the circumferential direction and the elimination of shadows, but such additional image processing may limit the speed at which the inspection system can process images.

The above-incorporated patent application describes that it may be desirable to make the inspection images fall on a particular portion of the camera screen. Such placement of the images enables the system to easily combine the signal of the image captured from the first camera with the signal of the image from the second camera (e.g., through the use of a simple multiplexer). The camera boxes of the above-incorporated patent application accomplish image placement by varying the locations and angles of the apertures and mirrors of the image capturing system. Unfortunately, this may require that each of the two cameras of the inspection system be unique, for each must have different locations and angles for its apertures and mirrors.

It would therefore be desirable to provide camera boxes that have a separate housing for the lens arrangement, with the separate housing having the capability to interface with a video camera at different angles in addition to straight in-line.

It would also be desirable to provide camera boxes that can are sealed to prevent contamination of the lens arrangement without interfering with the image capturing process.

It would further be desirable to provide camera boxes that provide still more illumination of the objects during inspection to further reduce the image processing requirements of the inspection system.

It would be still further desirable to provide camera boxes which are adjustable, such that the position of the received image can be varied within the camera screen without affecting the lens arrangement.

SUMMARY OF THE INVENTION

In view of the foregoing, it is an object of this invention to provide systems for inspection which include camera boxes that have a separate housing for the lens arrangement, with the separate housing having the capability to interface with a video camera at different angles in addition to straight in-line.

It is also an object of this invention to provide systems for inspection which include camera boxes that may be sealed to prevent contamination of the lens arrangement without interfering with the image capturing process.

It is an additional object of the invention to provide systems for inspection which include camera boxes that provide still more illumination of the objects during inspection to reduce the image processing requirements of the inspection system.

Furthermore, it is an object of the invention to provide systems for inspection which include adjustable camera boxes, such that the position of the received image can be varied within the camera screen without affecting the lens arrangement.

These and other objects of the invention are accomplished in accordance with the principles of the invention by providing improved camera boxes for optically inspecting surfaces. The improved camera boxes include a lens arrangement located within a self-contained housing which is separate from the camera. The camera boxes also include adjustment capability between the camera and the housing such that the position of the captured image on the camera screen can be varied without affecting the lens arrangement. Such an arrangement provides increased flexibility during installation of the camera boxes within the inspection system. The self-contained units are sealed units having a light receiver to receive light from the illuminated object while preventing contaminating particles from entering the housing. The light receiver is implemented such that it will also remain free of particle contamination with little or no maintenance.

The camera boxes of the present invention are provided with illuminator windows which enable the improved camera boxes to utilize additional light arrays. The preferred embodiment of the present invention uses four light arrays to illuminate the objects being inspected. The additional light arrays provide a higher quantity of light which provides for more uniform illumination.

Further features of the invention, its nature and various advantages will be more apparent from the accompanying drawings and the following detailed description of the preferred embodiments.

BRIEF DESCRIPTION OF THE DRAWINGS

The above and other objects and advantages of the invention will become apparent upon consideration of the following detailed description, taken in conjunction with the accompanying drawings, in which like reference characters refer to like parts throughout, and in which:

FIG. 4 is a longitudinal cross-sectional view of the illuminator window of FIG. 2, taken from line 4—4 of FIG. 2.

FIG. 5 is another cross-sectional view of the illuminator window of FIG. 2, taken from line 5—5 of FIG. 2.

FIG. 6 is a perspective view of the illuminator window of FIG. 2.

FIG. 17 is a schematic diagram of an alternative embodiment of the present invention using two of the devices of FIG. 1.

DETAILED DESCRIPTION OF THE INVENTION

Figure 1:
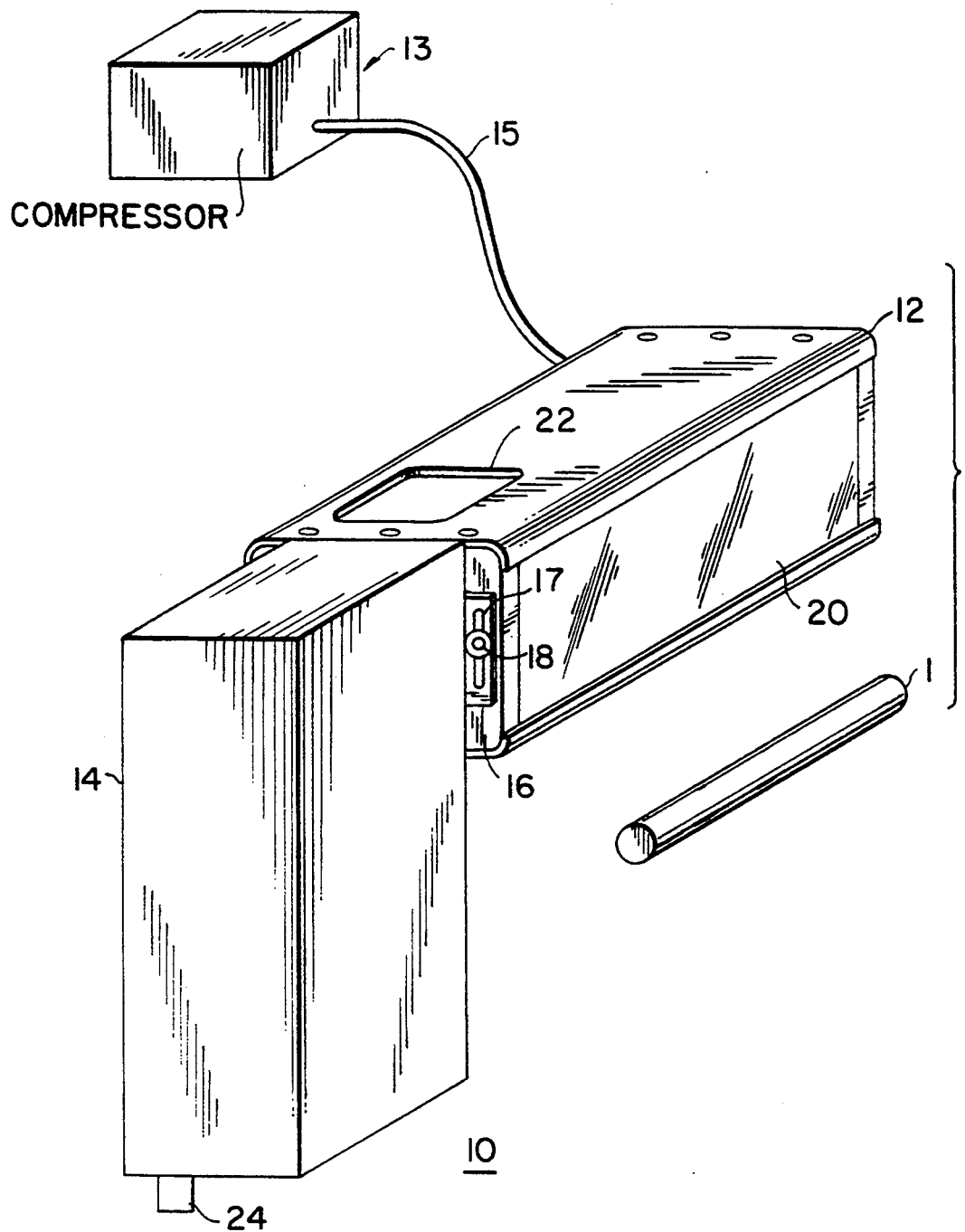
FIG. 1 is a perspective view of a camera box inspecting a cigarette according to the present invention.

FIG. 1 shows a perspective view of camera box 10, the preferred embodiment of the present invention. The camera boxes are used to optically inspect the cylindrical surface of articles during manufacturing, one such article typically being cigarette 1. Camera box 10 comprises two main components, lens arrangement housing 12 and camera housing 14. Housing 12 contains a lens and mirror arrangement which is shown is greater detail in FIG. 3. Camera housing 14 is movably mounted to housing 12 through the use of aperture 17 within brackets 16 and locking screws 18, the purpose of which is described more fully below. Brackets 16 can be fixedly mounted to housing 14 or they can be directly formed as part of housing 14. Camera housing 14 also includes electrical connector 24 through which electrical power is supplied to the camera and image signals are passed on for further processing.

Figure 2:
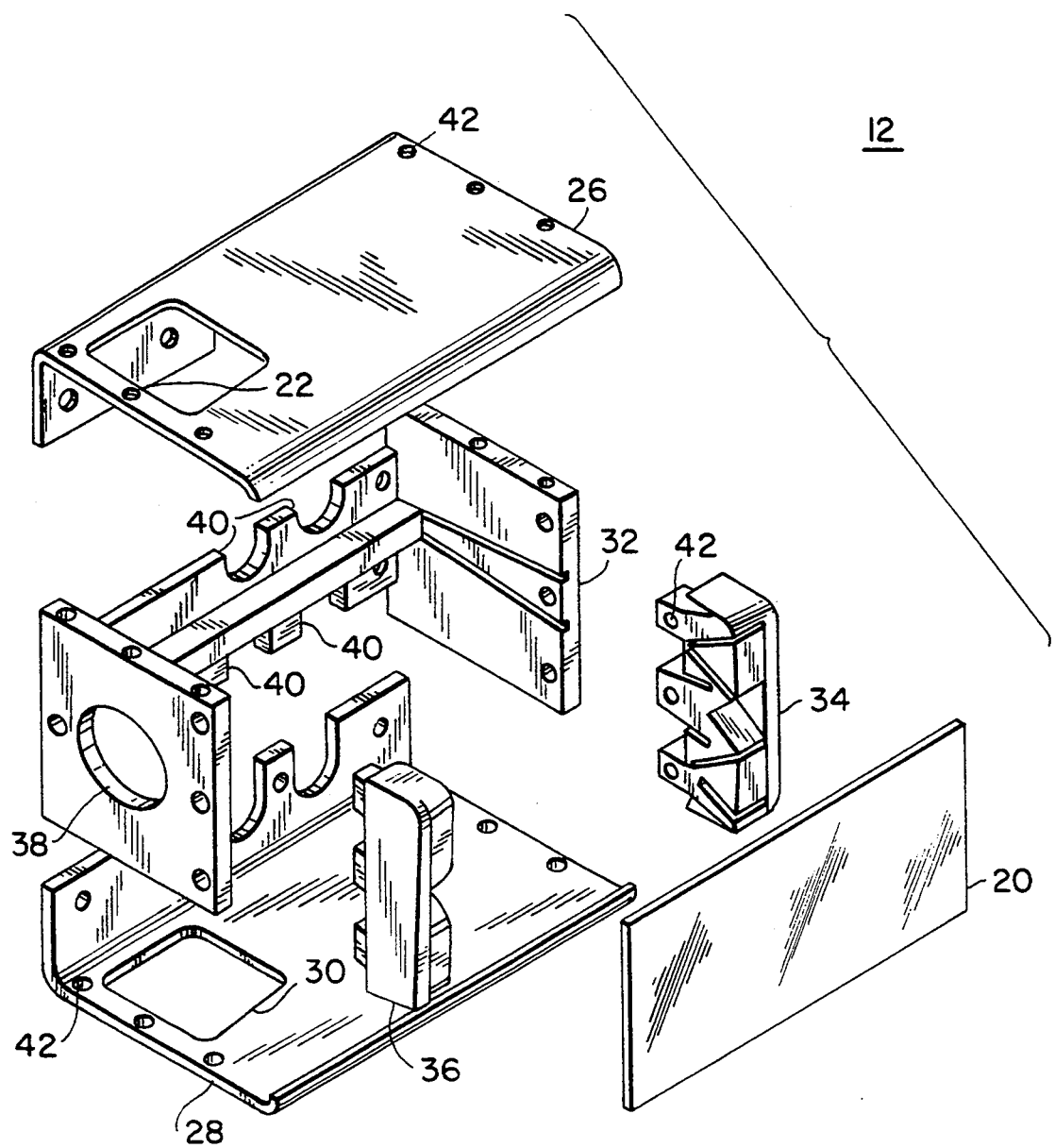
FIG. 2 is an exploded view of the housing for the lens arrangement of the camera box of FIG. 1.

FIG. 2 shows lens arrangement housing 12 in greater detail. Housing 12 is comprised of top shell 26, which includes aperture 22 to provide access for adjusting the camera lens, bottom shell 28 (and similar adjustment aperture 30), mounts 34 and 36, frame 32, and front window 20. Mounts 34 and 36 are used to install the lens and mirror arrangement of FIG. 3 within housing 12. Frame 32 includes camera lens aperture 38 and four apertures 40 through which fiber optic cables pass (as described below). Shells 26 and 28, and mounts 34 and 36 are attached to frame 32 by any conventional means, such as screws or bolts (not shown) going through openings 42.

During normal operation, all of the apertures are sealed to prevent contamination of the lens and mirror arrangement. As an additional preventative measure, positive air pressure can be applied from compressor 13 (or other conventional means) to housing 12 through hose 15 (see FIG. 1) to further prohibit the introduction of contaminants to the lens arrangement. Also to prohibit contamination, front window 20 is preferably coated with a conductive substance, which is electrically grounded, to prevent window 20 from becoming charged by the high speed air flow as cigarettes 1 pass in front of window 20. Therefore, particles are prevented from adhering to the window.

Figure 3:
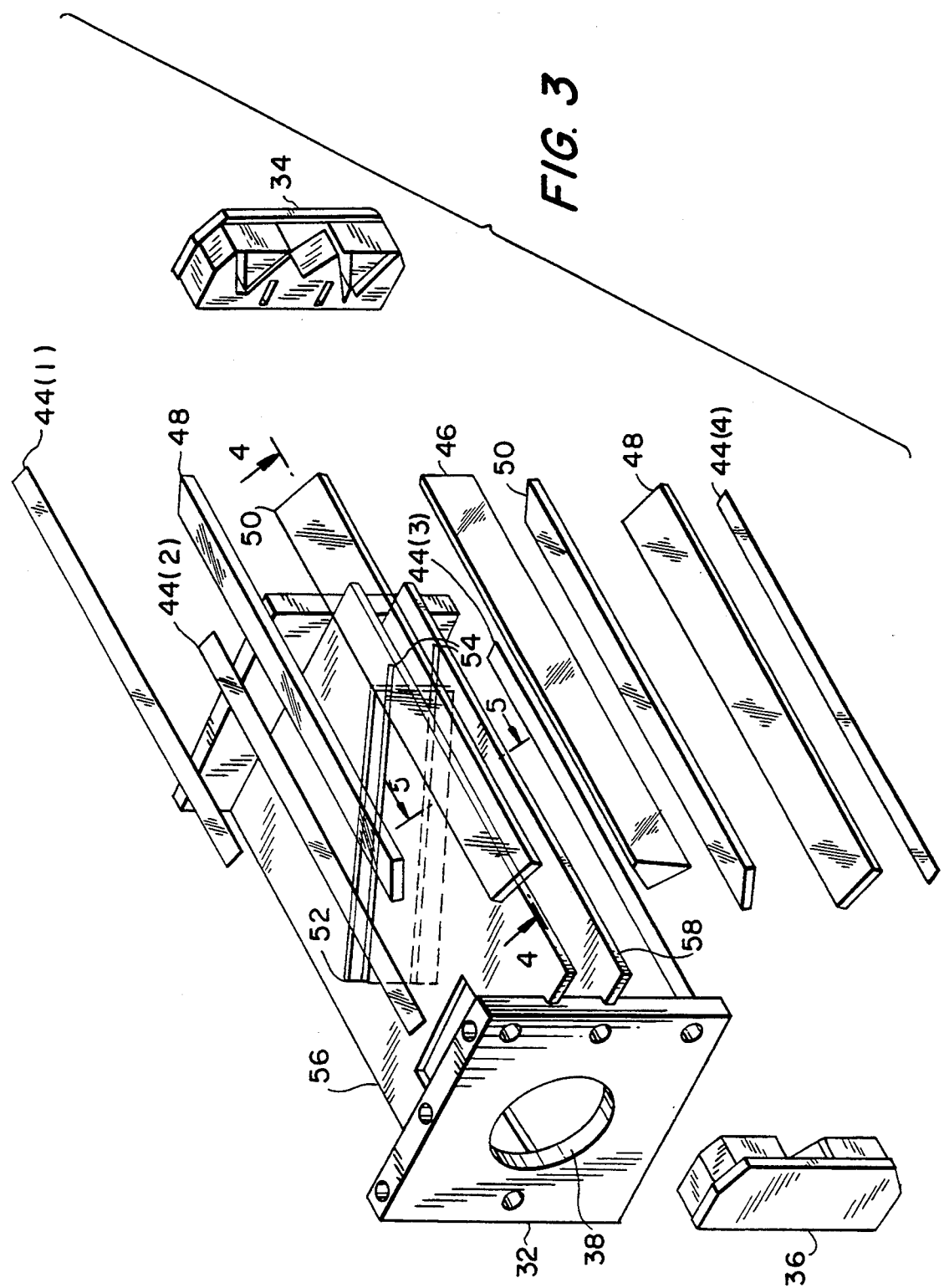
FIG. 3 is an exploded view of the internal lens arrangement within the housing of FIG. 2.

FIG. 3 shows elements of a lens and mirror arrangement according to the preferred embodiment of the present invention. As previously stated, mounts 34 and 36 are attached to frame 32, all of which contain slots to hold support members 56 and 58 (as shown in FIG. 3). Camera box 10 more fully illuminates cigarette 1 by employing two additional fiber optic illuminators 44(2) and 44(3) in addition to fiber optic illuminators 44(1) and 44(4). All of the fiber optic illuminators are constructed in essentially the same manner as the light sources described in U.S. patent application 07/884,746.

The present application utilizes the additional illuminators through the use of illuminator windows 50 (which are shown in more detail in FIGS. 4–6, and described below). Fiber optic illuminators 44(2) and 44(3) are mounted to the longitudinal edge of each illuminator window 50 such that illuminator window 50 acts as a light pipe. Both surfaces of window 50 are coated to provide total internal reflection within the light pipe. Additionally, all of the side edges of window 50 are polished. In this manner, light can be transmitted through the edges of window 50 in a first direction to further illuminate cigarette 1. The reflected image can pass through the coated surfaces of window 50 in a second, perpendicular, direction, without a significant loss of resolution in the image. The use of illuminator windows 50 enables the present invention to supply additional and more even illumination to cigarette 1.

Figure 10:
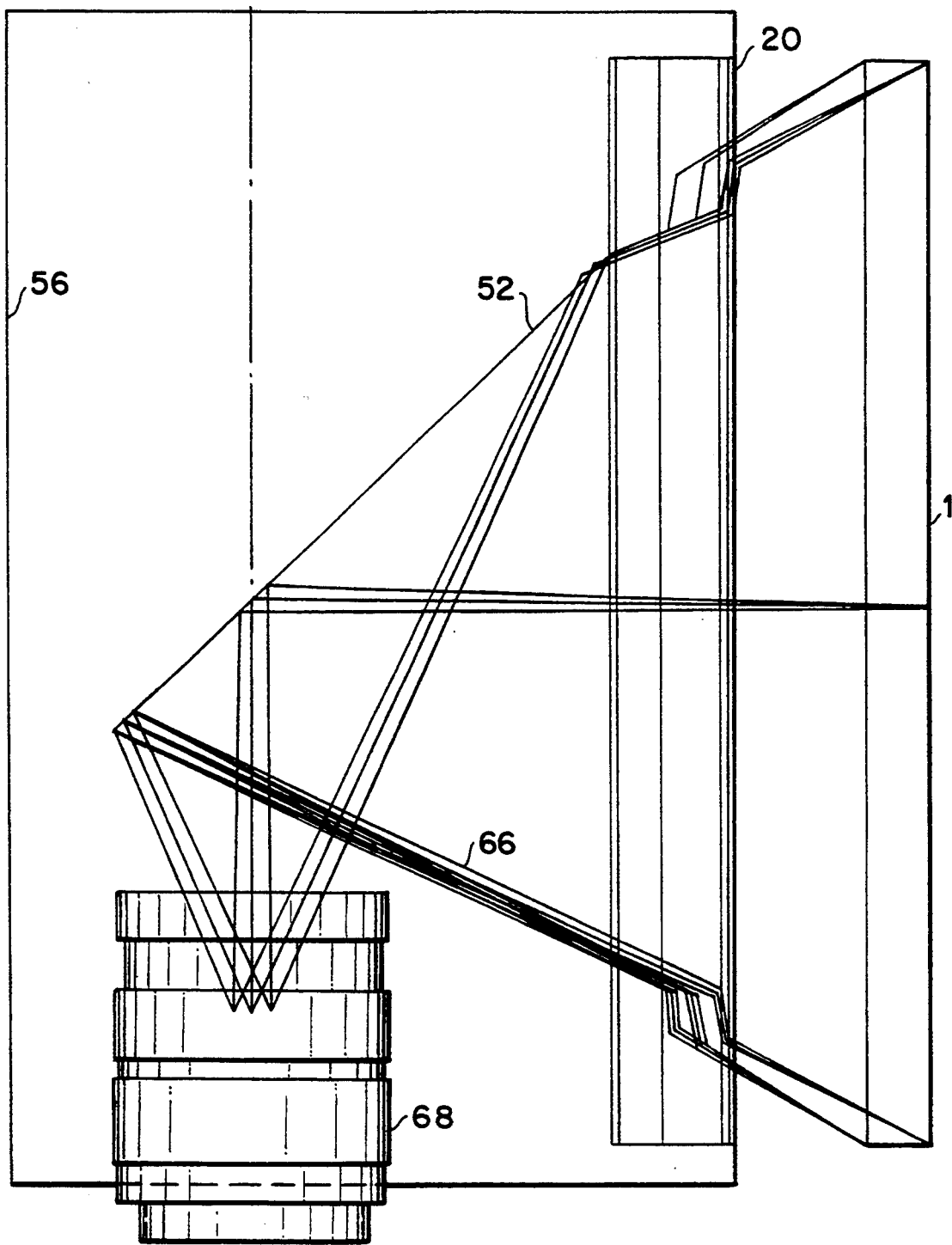
FIG. 10 is a schematic top-view showing the right-angle camera installation of the preferred embodiment of the present invention.
Figure 11:
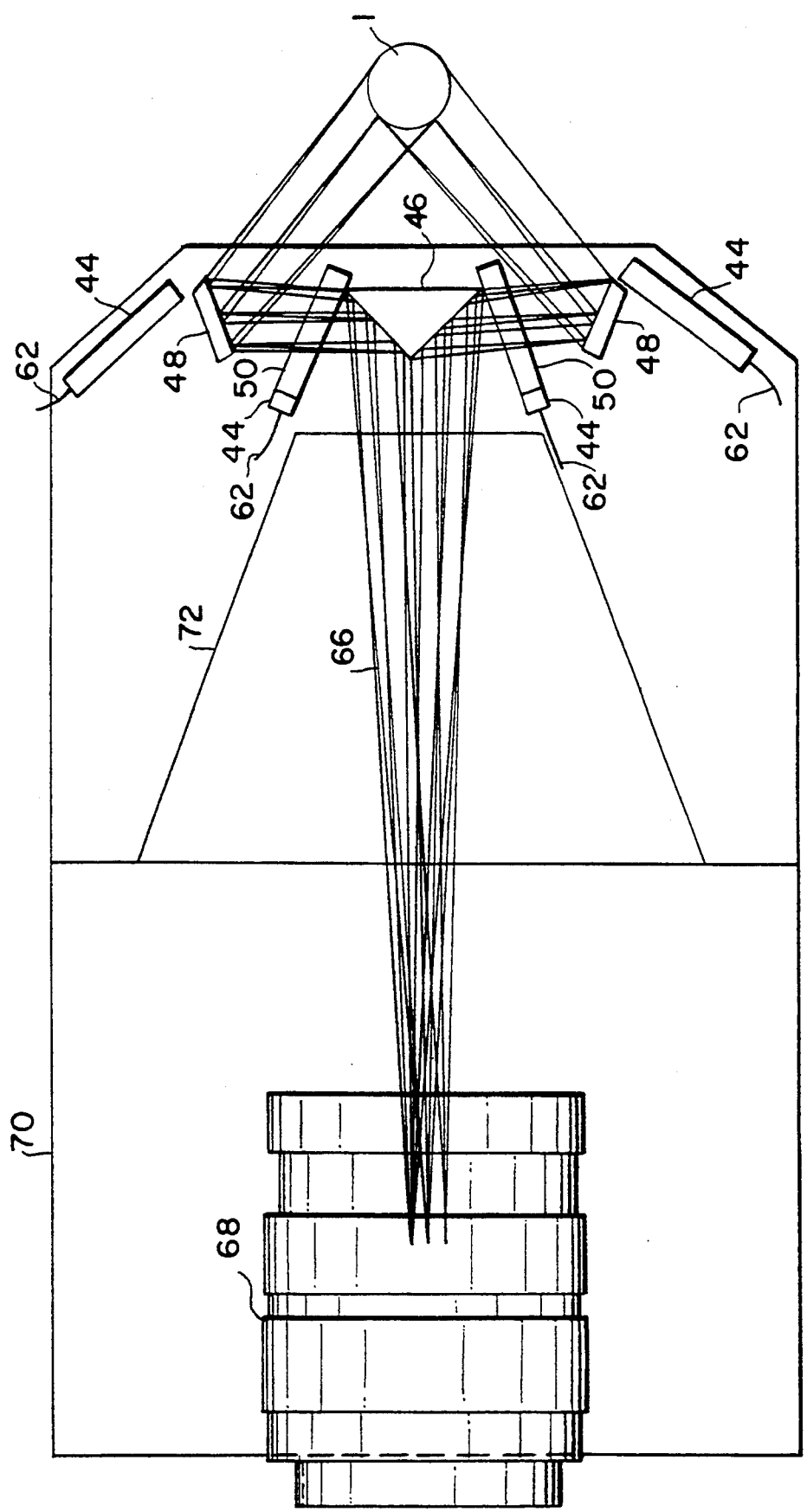
FIG. 11 is a schematic plan-view showing the straight in-line installation of an alternative embodiment of the present invention.

The upper illuminators (44(1) and 44(2)) cause a first subimage of cigarette 1 to be created, while the lower illuminators (44(3) and 44(4)) cause a second, distinct, subimage to be created. Some overlap of illumination may also occur. The illuminated subimages are first received by the corresponding upper and lower mirrors 48 of camera box 10. The mirrors reflect the subimages though the appropriate illuminator window 50. The subimages pass through the appropriate upper and lower windows 50 to prism 46 which provides additional reflection of the separate subimages. From prism 46, both the upper and lower subimages are reflected to folding mirror 52. Folding mirror 52 reflects the subimages into aperture 38, which is occupied by camera lens 68 (as shown in FIGS. 10 and 11).

The arrangement of mirrors, windows and prism is maintained by mounts 34 and 36 which contain holding slots in the same manner as frame 32. Upper and lower mirrors 48, upper and lower illuminator windows 50, and prism 46 are all held in place in the slots of mounts 34 and 36, as shown in FIG. 3. Folding mirror 52 is mounted within slots 54 in upper support member 56 and lower support member 58. This arrangement of illuminators and mirrors enables the present invention to more fully illuminate the object under inspection. Additionally, by separating the lens and mirror housing from the camera, housing 12 can be implemented in a much more compact manner, thereby permitting easier and more flexible installations within the overall inspection system.

FIGS. 4–6 show illuminator window 50 and its operation. FIGS. 4 and 5 show suggested dimensions of the illuminator window of the preferred embodiment, but are not meant to limit the scope of the invention. Fiber optic cable 60 is formed from a plurality of subcables (as shown in FIG. 4). Each subcable is comprised of a plurality of optical fibers which transmit light. The fibers may be terminated in fiber optic illuminator 44 as described in U.S. patent application 07/884,746. Illuminator 44 is mounted to illumination window 50 such that a minimum, if any, loss of light occurs at the transfer point. The illumination light is transmitted along fibers 62 into illuminator 44 and through window 50, at which point they exit window 50 as shown by light rays 64.

Figure 7:
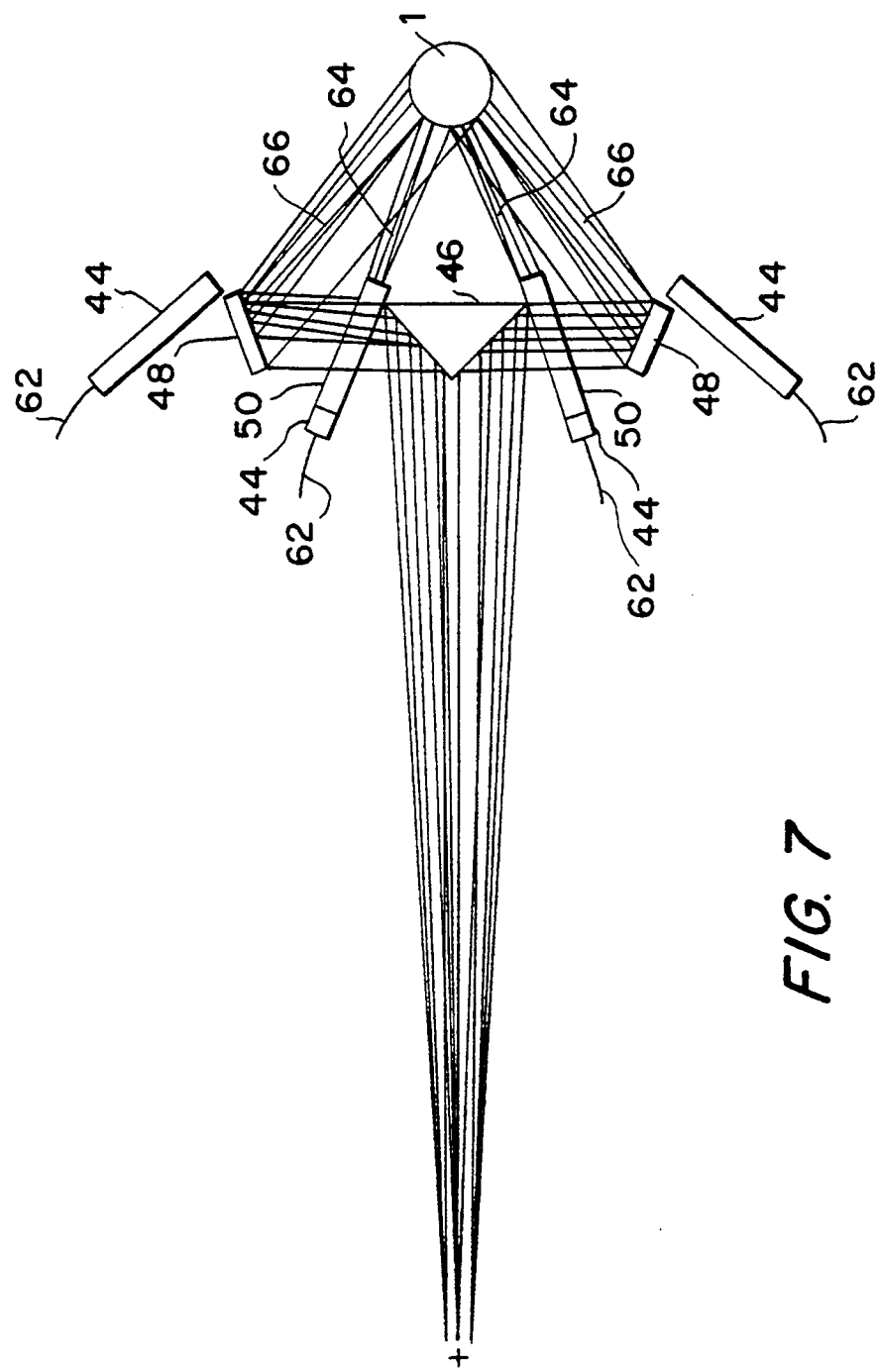
FIG. 7 is a schematic view showing the operation of the illuminator windows of FIG. 2.

The light rays provide a more even illumination of the surface of cigarette 1. As previously described, the subimages of cigarette 1 are captured by mirrors and reflected through windows 50 in the form of light ray 66 (shown most clearly in FIGS. 5 and 7). FIG. 7 shows illuminating rays 64 leaving window 50 and being directed to cigarette 1. The reflected image, in the form of light rays 66, is captured by mirrors 48 and reflected through window 50 to prism 36. Prism 36 takes each of the subimages and directs it to a central focal point. This focal point may occur at folding mirror 52 or it may occur directly in the camera lens.

Figure 8:
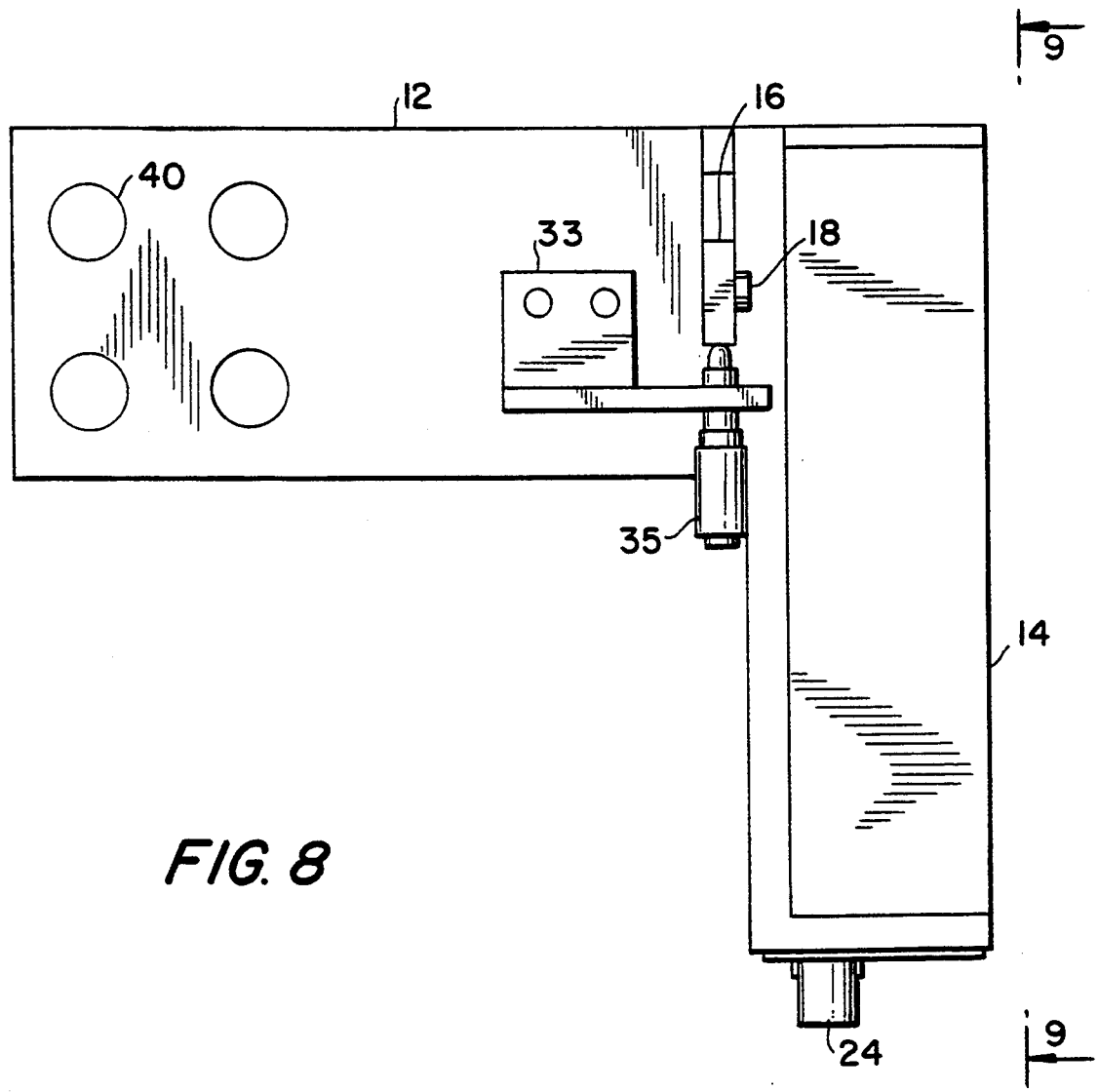
FIG. 8 is a schematic plan-view showing the right-angle camera installation of the preferred embodiment of the present invention.
Figure 9:
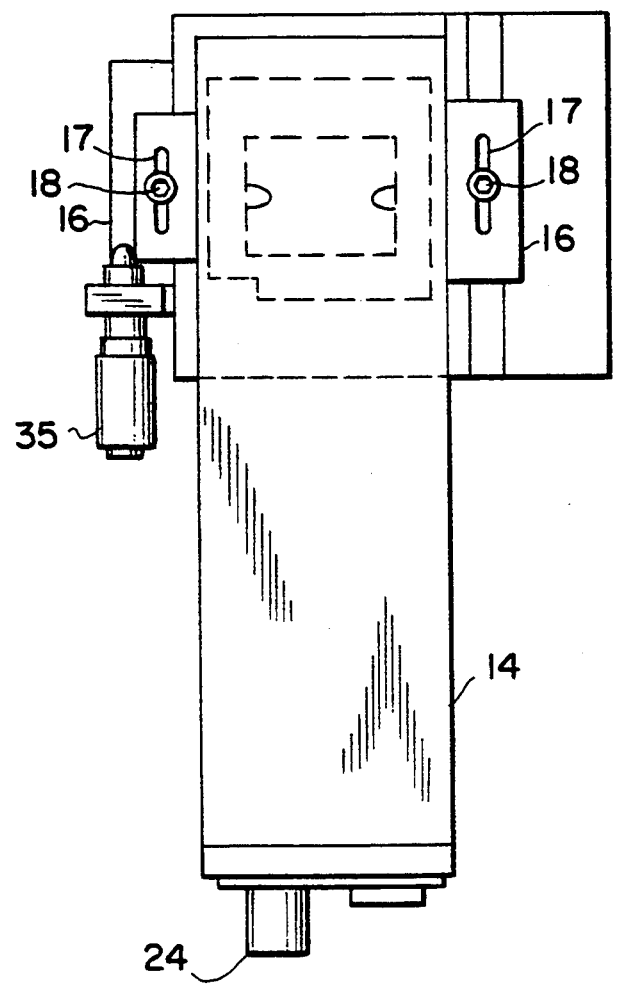
FIG. 9 is a schematic side-view showing the right-angle camera installation taken from line 9—9 of FIG. 8.

FIGS. 8 and 9 show the mounting between lens arrangement housing 12 and camera housing 14. FIG. 8 shows an additional mounting bracket 33 which is fixedly attached to the back of housing 12 by conventional means. Bracket 33 is designed so that it may hold micrometer 35. If micrometer 35 is installed in bracket 33, it will be in contact with bracket 16 of camera housing 14. In the preferred embodiment of the present invention, aperture 17 permits housing 14 to move approximately one quarter inch relative to housing 12 during installation. This movement is accomplished by adjusting micrometer 35 up or down, as necessary. After screws 18 have been used to secure housing 14 to housing 12, micrometer 35 may be removed.

The movable mounting design permits a single camera/housing unit to be used for both camera boxes in the overall inspection system of U.S. patent application 07/884,746. Additionally, the mounting design of the present invention enables the user to physically direct the position of the received image on the video camera. This eliminates the processing that may be required to place the images received by each camera in the overall inspection system. More simply, by physically adjusting where the focal point of the image enters the video lens of each camera, the image from the first camera can be positioned to occur above the location where the received image of the second camera occurs. This enables the inspection system to merge the two images without any further processing to form the complete inspection image. A sample implementation of this concept is shown in FIG. 17 and described below.

FIGS. 10 and 11 show alternate embodiments of the present invention, with FIG. 10 showing the preferred embodiment of a right angle camera installation and FIG. 11 showing an alternative embodiment of an in-line installation. FIG. 10 shows the folding of light rays 66 that occurs from the use of the mirrors and prism to form the final image. FIG. 11 shows alternate housing 70 containing an in-line installation, where a folding mirror is not utilized, which includes light baffle 72 to eliminate unwanted reflections. Both FIGS. 10 and 11 show camera lens 68 being inserted through its aperture, into the lens and mirror housing, as it would be during normal use.

Figure 12:
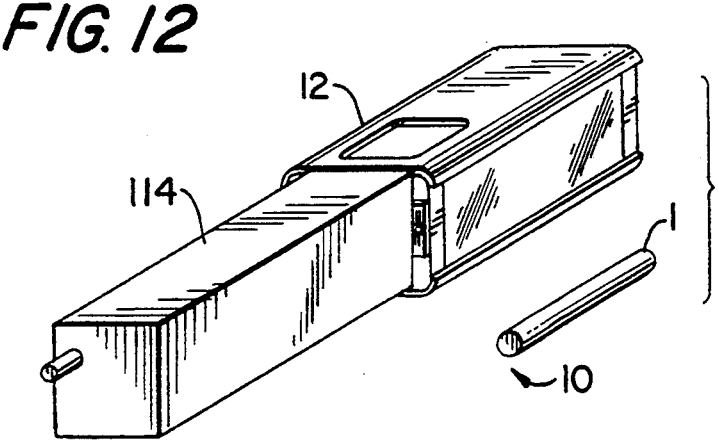
FIG. 12 is a simplified perspective view of an alternative embodiment of camera box inspecting a cigarette according to the present invention.
Figure 13:
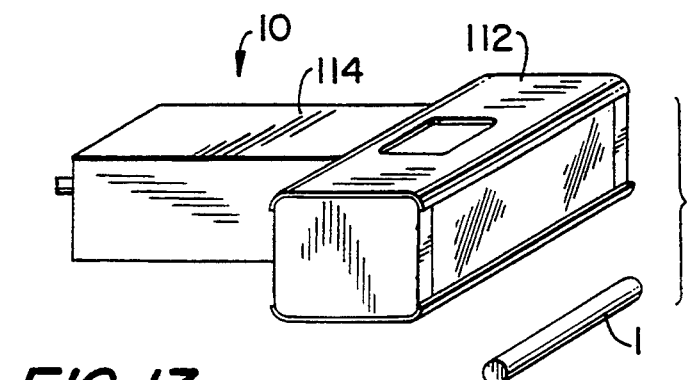
FIG. 13 is a simplified perspective view of another alternative embodiment of camera box inspecting a cigarette according to the present invention.
Figure 14:
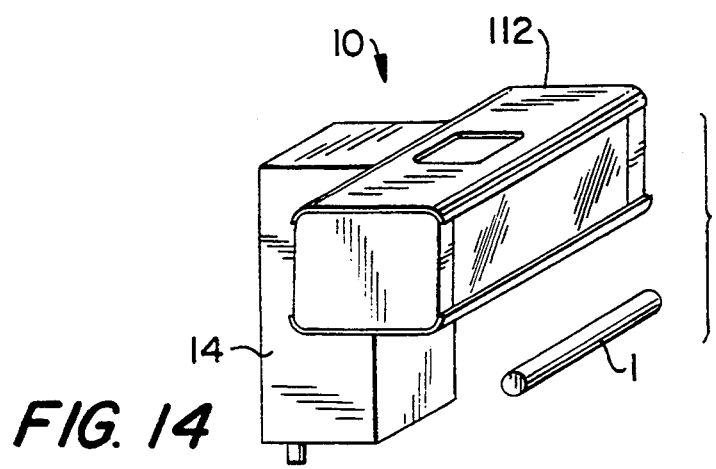
FIG. 14 is a simplified perspective view of still another alternative embodiment of camera box inspecting a cigarette according to the present invention.

FIGS. 12–14 show some of the different installation configurations that are possible using camera box 10. To achieve some of those configurations, it will be apparent to those skilled in the art that an alternative, in-line, camera housing 114 may be used instead of camera housing 14. Where housing 14 provides a right angle between lens 68 and a conventional video camera (not shown), housing 114 provides a straight in-line configuration. By combining the different configurations (in-line and right angle) of lens arrangement housings and camera housings to form camera box 10, camera box 10 gives the user greatly increased flexibility for installation. FIG. 12 shows a configuration using right angle lens arrangement housing 12 and in-line camera housing 114. FIG. 13 shows an installation where both in-line housings 112 and 114 are used. FIG. 14 shows another installation using in-line housing 112, but with right angle camera housing 14 instead of camera housing 114.

Figure 15:
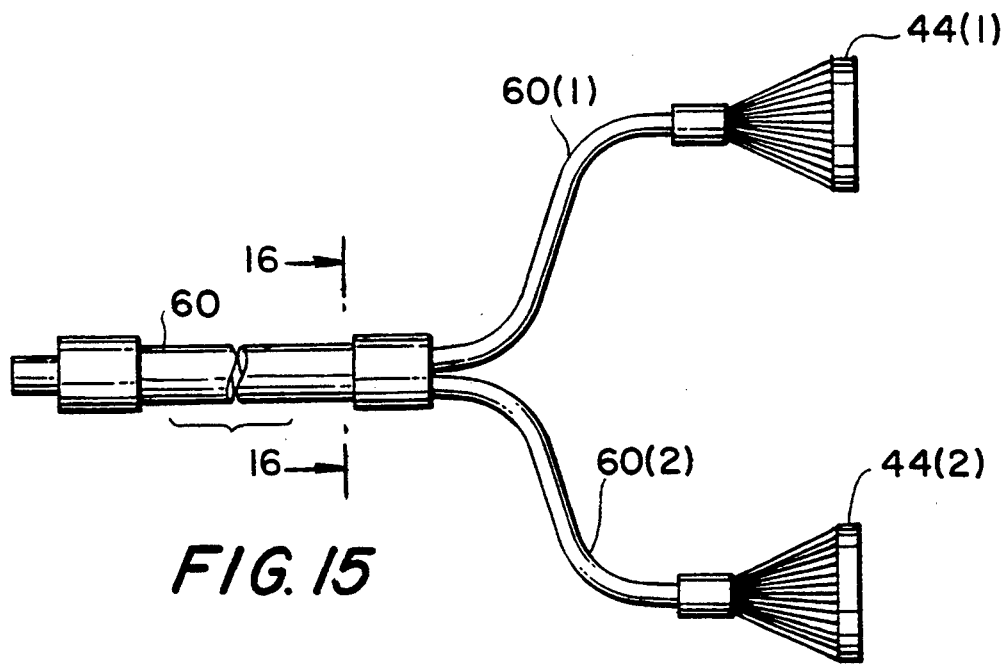
FIG. 15 is a schematic view of the fiber-optic cable/illuminator window installation in accordance with the principles of the present invention.
Figure 16:
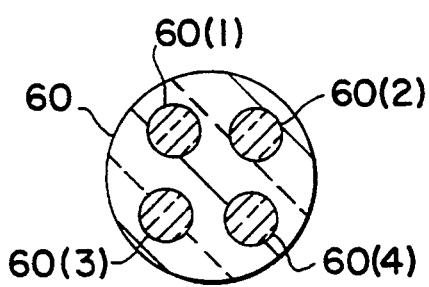
FIG. 16 is a radial cross-sectional view of the fiber-optic cables of FIG. 15, taken from line 16—16 of FIG. 15.

FIG. 15 shows a schematic view of fiber optic cable 60 of the present invention. In the preferred embodiment, fiber optic cable 60 is formed from four subcables, one for each illuminator 44. Fiber optic cable 60 is constructed to accommodate the installation within housing 12. As previously described, the subcables enter housing 12 through apertures 40, which are arranged in pairs. The upper two apertures 40 receive the subcables for illuminators 44(1) and 44(2), while the lower apertures receive the subcables for illuminators 44(3) and 44(4). Therefore subcable 60(1) overlies subcable 60(3)

and subcable 60(2) overlies subcable 60(4). FIG. 16 is a cross-sectional view of cable 60 showing all four subcables.

FIG. 17 shows an embodiment of the present invention where two instances of camera box 10 are utilized in a complete inspection system. The first camera box 10(1) is used to capture a first pair of subimages which collectively correspond to at least 180° of a first side of cigarette 1. A second camera box 10(2) is utilized to capture a second pair of subimages which collectively corresponding to at least 180° of the other side of cigarette 1. A complete description of a system to support and rotate the cigarettes during inspection is provided in U.S. patent application 07/884,746. The first and second pairs of subimages are then merged by image merger 65 into final image 70 of cigarette 1. Image merger 65 may be a conventional multiplexer or other means.

This embodiment emphasizes the advantages of the adjustable mounting between housing 12 and housing 14 of the camera box. The adjustable mounting enables two identical camera boxes to be used to capture two pairs of subimages at different positions in the final image without requiring any additional image processing. For example, the first camera box 10(1) is manually adjusted using micrometer 35 to position the first pair of subimages in the top portion of the photosensitive area of the video camera. The second camera box 10(2) is also manually adjusted using micrometer 35, but the position of the second pair of subimages is in the lower portion of the photosensitive area of the video camera. In this manner, image merger 65 can simply combine the two pairs of subimages into a final image and no image processing to reposition the pairs of subimages is required.

It will be understood that the foregoing is merely illustrative of the principles of this invention, and that various modifications can be made by those skilled in the art without departing from the scope and spirit of the invention. For example, by utilizing additional illuminator windows, larger sized objects can be fully illuminated for inspection without interfering with the capturing of the necessary reflections of the images. Alternatively, more than two cameras might be utilized to optically inspect more complex objects.

The invention claimed is:

1. Apparatus for forming an image during optical inspection of substantially the entire circumference of the cylindrical surface of a cylindrical object, the apparatus comprising:

a first housing having a front window, said first housing containing a plurality of illuminators for illuminating said cylindrical surface through said window, a plurality of reflectors for receiving illumination reflected from said surface and for guiding said illumination to a central location to form said image, and a plurality of illumination windows mounted to selected illuminators for providing increased illumination of said cylindrical surface through said window without interfering with said reflected illumination such that no significant loss of resolution in the image occurs, wherein said illuminator windows provide said illumination substantially completely through said illuminator windows alone a first axis and pass said reflected illumination substantially completely through said illuminator windows alone a second orthogonal axis;

a second housing containing a video camera which has a lens for receiving said image and a photosensitive area comprising at least two portions; and adjustable mounting for adjustably mounting said second housing to said first housing and providing said lens at said central location such that said image is formed on a predetermined portion of the at least two portions of said photosensitive area of said video camera.

2. The apparatus defined in claim 1, wherein said first housing is a substantially sealed unit to prevent contamination of said illuminators and said reflectors.

3. The apparatus defined in claim 1, wherein said first housing further includes means for maintaining within said first housing a positive air pressure relative to ambient atmospheric air pressure.

4. The apparatus defined in claim 3, wherein said window is coated with a transparent conductive coating which is grounded to prevent contaminant particles from adhering to said window.

5. The apparatus defined in claim 1, wherein said central location is located along a first axis which extends from the center of, and is perpendicular to, the longitudinal axis of said cylindrical object to accommodate a straight in-line camera.

6. The apparatus defined in claim 1, wherein said central location is offset from a first axis which extends from the center of, and is perpendicular to, the longitudinal axis of said cylindrical object, said offset being accomplished to accommodate a camera having a nonzero angular relationship between said lens and a photosensitive area within said camera.

7. The apparatus defined in claim 6, wherein said first housing further contains an additional reflector for reflecting said illumination to said offset location.

8. The apparatus defined in claim 1, wherein said adjustable mounting comprises:

a removable micrometer for applying precision control adjustment to said adjustable mounting; and a pair of mounting brackets fixedly attached to said second housing, said brackets substantially restricting said adjustment movement to a single axis by having an elongated aperture along said single axis.

9. The apparatus defined in claim 8, wherein said adjustable mounting further comprises a pair of attachment bolts for removably fixing said second housing to said first housing after adjustment by said micrometer, said bolts extending through said elongated aperture into said first housing.

10. The apparatus defined in claim 1, wherein said first housing further includes lens adjustment apertures for adjusting said lens and lens adjustment aperture covers for closing said lens adjustment apertures.

11. The apparatus according to claim 1, wherein each illuminator window functions as a light pipe having upper and lower surfaces coated to provide total internal reflection.

12. The apparatus according to claim 11, wherein side edges of each illuminator window are polished.

13. Apparatus for forming an image during optical inspection of substantially the entire circumference of the cylindrical surface of a cylindrical object, the apparatus comprising:

a first housing comprising a frame member, top and bottom wall members attached to said frame member, and a front window mounted to said top and bottom members, said first housing containing four illuminators for illuminating said cylindrical surface through said window, two reflective mirrors and a prism for receiving illumination reflected from said surface and for guiding said illumination to a central location to form said image and a plurality of illuminator windows mounted to selected illuminators for providing increased illumination of said cylindrical surface through said window without interfering with said reflected illumination such that no significant loss of resolution in the image occurs wherein said illuminator windows provide said illumination substantially completely through said illuminator windows alone a first axis and pass said reflected illumination substantially completely through said illuminator windows along a second orthogonal axis;

a second housing containing a video camera which has a lens for receiving said image and a photosensitive area having at least two portions; and adjustable mounting for adjustably mounting said second housing to said first housing and providing said lens at said central location such that said image is formed on a predetermined portion of the at least two portions of said photosensitive area.

14. The apparatus of claim 13, wherein said image is formed of two subimages, each subimage representing at least 90° of one side of said surface of said cylindrical object.

15. The apparatus of claim 14, wherein each subimage is formed by said illumination from said illuminators being reflected from said surface of said cylindrical object into one of said reflective mirrors, said illumination then being guided by said mirror to one side of said prism, said prism then guiding said illumination to said central location, such that two subimages exist at said central location.

16. The apparatus of claim 15, wherein said first housing further includes a folding mirror for moving said subimages at said central location to a location offset from a first axis which extends from the center of, and is perpendicular to, the longitudinal axis of said cylindrical object, said offset being accomplished to accommodate a camera having a non-zero angular relationship between said lens and a photosensitive area within said camera.

17. The apparatus according to claim 13, wherein each illuminator window functions as a light pipe having upper and lower surfaces coated to provide total internal reflection.

18. The apparatus according to claim 17, wherein side edges of each illuminator window are polished.

19. Apparatus for forming an image during optical inspection of substantially the entire circumference of the cylindrical surface of a cylindrical object, the apparatus comprising:

a first housing having a window, said first housing containing a plurality of illuminators for illuminating at least 180° of a first side of said cylindrical surface through said window, a plurality of reflectors for receiving said first illumination reflected from said surface and for guiding said first illumination to a first central location to form a first pair of subimages which collectively represent at least 180° of a first side of said cylindrical surface and a plurality of illuminator windows mounted to selected illuminators for providing increased illumination of said cylindrical surface through said window without interfering with said reflected illumination such that no significant loss of resolution in the image occurs, wherein said illuminator windows provide said illumination substantially completely through said illuminator windows along a first axis and pass said reflected illumination substantially completely through said illuminator windows; along a second orthogonal axis;

a second housing containing a first video camera which has a first lens for receiving said first pair of subimages and a first photosensitive area comprising first and second portions; and first adjustable mounting for adjustably mounting said second housing to said first housing and providing said first lens at said first central location such that said first pair of subimages is formed on the first portion of said first photosensitive area of said first video camera;

a third housing having a window, said third housing containing a plurality of illuminators for illuminating at least 180° of the other side of said cylindrical surface through said third housing window, a plurality of reflectors for receiving said second illumination reflected from said surface and for guiding said second illumination to a second central location to form a second pair of subimages which collectively represent at least 180° of the other side of said cylindrical surface, and a plurality of illuminator windows mounted to selected illuminators for providing increased illumination of said cylindrical surface through said window without interfering with said reflected illumination such that no significant loss of resolution in the image occurs, wherein said illuminator windows provide said illumination substantially completely through said illuminator windows along a first axis and pass said reflected illumination substantially completely through said illuminator windows alone a second orthogonal axis;

a fourth housing containing a second video camera which has a second lens for receiving said second pair of subimages and a second photosensitive area comprising first and second portions which respectively correspond to the first and second portions of said first photosensitive area of said first video camera; and second adjustable mounting for adjustably mounting said fourth housing to said third housing and providing said second lens at said second central location such that said second pair of subimages is formed on the second portion of said second photosensitive area of said second video camera; and an image merger for merging said first and second pairs of subimages into said image, said first and second adjustable mountings being adjusted so that said first and second pairs of subimages are positioned in a non-overlapping manner within said image.

20. The apparatus according to claim 19, wherein each illuminator window functions as a light pipe having upper and lower surfaces coated to provide total internal reflection.

21. The apparatus according to claim 20, wherein side edges of each illuminator window are polished.

22. Apparatus for forming an image during optical inspection of substantially the entire circumference of the cylindrical surface of a cylindrical object, comprising:

a plurality of illuminators for illuminating the cylindrical surface, a plurality of illuminator windows located between some of said illuminators and in the illumination path of other illuminators for providing increased illumination of the cylindrical surface along a first axis of each of said illuminator windows, the illuminator windows passing illumination from the cylindrical surface substantially completely through the illuminator windows along a second orthogonal axis of each of said illuminator windows, and a plurality of reflectors for receiving the reflected illumination and for guiding the illumination to a central location to form the image, wherein the reflected illumination along the second orthogonal axis passes through the provided increased illumination along the first axis without a significant loss of resolution in the formed image.

23. Apparatus according to claim 22, wherein the central location is located along an axis which extends from the center of, and is perpendicular to, the longitudinal axis of said cylindrical object to accommodate a straight in-line camera.

24. Apparatus according to claim 22, wherein the central location is offset from an axis which extends from the center of, and is perpendicular to, the longitudinal axis of the cylindrical object, the offset being accomplished to accommodate a camera having a non-zero angular relationship between the lens and a photosensitive area within the camera.

25. Apparatus according to claim 24, wherein the housing further contains an additional reflector for reflecting the illumination to the offset location.

26. Apparatus according to claim 22, wherein each illuminator window functions as a light pipe having upper and lower surfaces coated to provide total internal reflection.

27. Apparatus according to claim 26, wherein side edges of each illuminator window are polished.

28. Apparatus for forming an image during optical inspection of substantially the entire circumference of the cylindrical surface of a cylindrical object, the apparatus comprising:

a first housing comprising a frame member, top and bottom wall members attached to said frame member, and a front window mounted to said top and bottom members, said first housing containing four illuminators for illuminating said cylindrical surface through said window, two reflective mirrors and a prism for receiving illumination reflected from said surface and for guiding said illumination to a central location to form said image, and a plurality of illuminator windows mounted to selected illuminators for providing increased illumination of said cylindrical surface through said window without interfering with said reflected illumination such that no significant loss of resolution in the image occurs, wherein each illuminator window functions as a light pipe having upper and lower surfaces coated to provide total internal reflection;

a second housing containing a video camera which has a lens for receiving said image and a photosensitive area having at least two portions; and adjustable mounting for adjustably mounting said second housing to said first housing and providing said lens at said central location such that said image is formed on a predetermined portion of the at least two portions of said photosensitive area.

29. The apparatus according to claim 28, wherein side edges of each illuminator window are polished.

30. Apparatus for forming an image during optical inspection of substantially the entire circumference of the cylindrical surface of a cylindrical object, the apparatus comprising:

a first housing having a window, said first housing containing a plurality of illuminators for illuminating at least 180° of a first side of said cylindrical surface through said window, a plurality of reflectors for receiving said first illumination reflected from said surface and for guiding said first illumination to a first central location to form a first pair of subimages which collectively represent all least 180° of a first side of said cylindrical surface , and a plurality of illuminator windows mounted to selected illuminators for providing increased illumination of said cylindrical surface through said window without interfering with said reflected illumination such that no significant loss of resolution in the image occurs, wherein each illumination window functions as a light pipe having upper and lower surfaces coated to provide total internal reflection;

a second housing containing a first video camera which has a first lens for receiving said first pair of subimages and a first photosensitive area comprising first and second portions; and first adjustable mounting for adjustably mounting said second housing to said first housing and providing said first lens at said first central location such that said first pair of subimages is formed on the first portion of said first photosensitive area of said first video camera;

a third housing having a window, said third housing containing a plurality of illuminators for illuminating at least 180° of the other side of said cylindrical surface through said third housing window, a plurality of reflectors for receiving said second illumination reflected from said surface and for guiding said second illumination to a second central location to form a second pair of subimages which collectively represent at least 180° of the other side of said cylindrical; surface, and a plurality of illuminator windows mounted to selected illuminators for providing increased illumination of said cylindrical surface through said window without interfering with said reflected illumination such that no significant loss of resolution in the image occurs,-wherein each illumination window functions as a light pipe having upper and lower surfaces coated to provide total internal reflection;

a fourth housing containing a second video camera which has a second lens for receiving said second pair of subimages and a second photosensitive area comprising first and second portions which respectively correspond to the first and second portions of said first photosensitive area of said first video camera; and second adjustable mounting for adjustably mounting said fourth housing to said third housing and providing said second lens at said second central location such that said second pair of subimages is formed on the second portion of said second photosensitive area of said second video camera; and an image merger for merging said first and second pairs of subimages into said image, said first and second adjustable mountings being adjusted so that said first and second pairs of subimages are positioned in a non-overlapping manner within said image.

31. The apparatus according to claim 30, wherein side edges of each illuminator window are polished.

32. Apparatus for forming an image during optical inspection of substantially the entire circumference of the cylindrical surface of a cylindrical object, the apparatus comprising:

a first housing having a front window, said first housing containing a plurality of illuminators for illuminating said cylindrical surface through said window, a plurality of reflectors for receiving illumination reflected from said surface and for guiding said illumination to a central location to form said image, and a plurality of illuminator windows mounted to selected illuminators for providing increased illumination of said cylindrical surface through said window without interfering with said reflected illumination such that no significant loss of resolution in the image occurs, wherein each illumination window functions as a light pipe having upper and lower surfaces coated to provide total internal reflection;

a second housing containing a video camera which has a lens for receiving said image and a photosensitive area comprising at least two portions; and adjustable mounting for adjustably mounting said second housing to said first housing and providing said lens at said central location such that said image is formed on a predetermined portion of the at least two portions of said photosensitive area of said video camera.

33. The apparatus according to claim 32, wherein side edges of each illuminator window are polished.

* * * * *